United States Patent
Mehta et al.

(10) Patent No.: US 12,016,857 B2
(45) Date of Patent: *Jun. 25, 2024

(54) STABLE LIQUID VIGABATRIN PHARMACEUTICAL COMPOSITION FOR ORAL DOSAGE

(71) Applicants: FTF PHARMA PRIVATE LIMITED, Ahmedabad (IN); LM MANUFACTURING LTD., Edgware (GB)

(72) Inventors: Sandip Mehta, Ahmedabad (IN); Manish Kumar Umrethia, Ahmedabad (IN); Jayanta Mandal, Ahmedabad (IN)

(73) Assignees: FTF PHARMA PRIVATE LIMITED, Ahmedabad (IN); LM MANUFACTURING LTD., Edgware (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,126

(22) Filed: May 2, 2023

(65) Prior Publication Data

US 2023/0263796 A1    Aug. 24, 2023

Related U.S. Application Data

(63) Continuation of application No. 17/299,844, filed as application No. PCT/IB2019/000979 on Aug. 16, 2019, now Pat. No. 11,738,020.

(30) Foreign Application Priority Data

Aug. 18, 2018 (IN) .............................. 201821030979

(51) Int. Cl.
| | |
|---|---|
| *A61K 31/4725* | (2006.01) |
| *A61K 31/197* | (2006.01) |
| *A61K 31/403* | (2006.01) |
| *A61K 31/4045* | (2006.01) |
| *A61K 47/12* | (2006.01) |

(52) U.S. Cl.
CPC ........ *A61K 31/4725* (2013.01); *A61K 31/197* (2013.01); *A61K 31/403* (2013.01); *A61K 31/4045* (2013.01); *A61K 47/12* (2013.01)

(58) Field of Classification Search
None
See application file for complete search history.

(56) References Cited

U.S. PATENT DOCUMENTS

| | | |
|---|---|---|
| 2006/0293382 A1 | 12/2006 | Weldele et al. |
| 2016/0166543 A1 | 6/2016 | Joshi et al. |

FOREIGN PATENT DOCUMENTS

| | | |
|---|---|---|
| CN | 108236608 A | 7/2018 |
| CN | 108853009 A | 11/2018 |
| WO | 2009112800 A1 | 9/2009 |

OTHER PUBLICATIONS

FDA Compliance Program Guidance Manual. Chapter 56—Drug Quality Assurance. Retrieved from the Internet on Dec. 4, 2023, https://www.fda.gov/media/75201/download. Published 2015. (Year: 2015).*
SciFinder, CN108236608 Substances. Retrieved from the internet on Dec. 28, 2022. (Year: 2022) (Year: 2022).*
"International Search Report and Written Opinion received for PCT Patent Application No. PCT/IB2019/000979, mailed on Jan. 21, 2020", 10 pages.
drugs.com , "Drug Expiration Dates—Are They Still Safe to Take?", Retrieved via Internet from https://web.archive.org/web/20171012053903/https://www.drugs.com/article/drug-expiration-dates.html, 2017, 2 pages.
pharmpress.com , "Pharmaceutical Solutions for Oral Administration", Oral Pharmaceutical Solutions, Chapter 1, 1644, Jul. 5, 2008, 24 pages.
RXLIST , "Sabril", The Wayback Machine, Retrieved form the Internet via https://web.archive.org/web/20180116050049/https://www.rxlist.com/sabril-drug.htm, 2018, 59 pages.
Nielsen, et al., "Vigabatrin Pediatric Dosing Information for Refractory Complex Partial Seizures: Results from a Population Dose-Response Analysis", Epilepsia, vol. 55, No. 12, 2014, pp. e134-e138.

* cited by examiner

*Primary Examiner* — Amy C Bonaparte
*Assistant Examiner* — Lauren Wells
(74) *Attorney, Agent, or Firm* — ADLER POLLOCK & SHEEHAN P.C.; Michel Morency

(57) ABSTRACT

This disclosure relates to pharmaceutical compositions in the form of a solution for oral delivery. Particularly, the pharmaceutical compositions comprise an active pharmaceutical ingredient, a buffering agent, and water. In some embodiments, the pH of the composition is from about pH 5 to about pH 8. In some embodiments, the active pharmaceutical ingredient is selected from ramipril, solifenacin, vigabatrin, losartan potassium, warfarin, and melatonin.

12 Claims, No Drawings

STABLE LIQUID VIGABATRIN PHARMACEUTICAL COMPOSITION FOR ORAL DOSAGE

This application is a continuation of U.S. application Ser. No. 17/299,844, filed on Jun. 4, 2021, which is a national phase filing under 35 U.S.C. § 371 of International Application No. PCT/IB2019/000979, which claims priority to Indian Provisional Application No. IN201821030979 filed on Aug. 18, 2018, entitled "PHARMACEUTICAL SOLUTION FOR ORAL DOSAGE," the contents of which are and is incorporated herein by reference.

BACKGROUND

This disclosure relates to pharmaceutical compositions in the form of a solution for oral delivery. Particularly, the pharmaceutical compositions comprise an active pharmaceutical ingredient, a buffering agent, and water. In some embodiments, the composition has improved stability and patient compliance. In some embodiments, the compositions may be advantageous for the patients having swallowing difficulties such as pediatric or geriatric patients or when the patients are unable to take solid oral dosage forms.

Syrups and suspensions are considered as favorable types of dosage forms in which to orally administer medicine to infants and children. However, they may have disadvantages such as solubility, a bad taste, portability problems or required refrigerator storage. World Health Organization (WHO) currently favors that infants and children be treated with oral solid medicines. New oral solid tablets, such as a mini-tablet, instead of liquid medicines are proposed for this group, however, there are few reports that mini-tablets are suitable for infants and children. Palatability is one of the main elements of patient acceptability of an oral pediatric medicine. Palatability is defined as the overall appreciation of an oral medicinal product in relation to its smell, taste, aftertaste and feeling in the mouth. Design of the formulation of an oral pediatric medicine should be considered together with its palatability.

Compared to conventional tablets and capsules, oral liquid dosage forms including solutions, syrups, suspensions, elixirs, and concentrates offer unique advantages to many patients. For example, liquids may provide better patient compliance for those with swallowing difficulties and better dosage control versus a fixed tablet dose. Hence, liquid dosage forms are generally formulated for use in geriatric and pediatric patients. However, there are also a number of "challenges" surrounding the formulation and development of these forms.

Oral liquids are formulated as solutions, suspensions and emulsions depending on the nature of the active ingredient particularly solubility and stability. They are also designed as ready to use liquids and powders for reconstitution into liquid orals like syrups, solutions, suspensions and emulsions. Liquid formulation needs various excipients including vehicle, solubilizer, stabilizer, and viscosity builder, preservatives, sweeteners, coloring agents and flavoring agents. The selection of these excipients is of major concern to design stable, effective and palatable oral liquid formulation.

Characteristics of active drug are of major concern in developing an oral liquid dosage formulation. The major challenges in developing oral liquid dosage forms are (i) the stability of a drug in solution, (ii) the solubility of a drug at the required level, and (iii) an acceptable taste. It is the effective use of excipients, which allows formulators to overcome these challenges. Additionally, an excipient's compatibility with a drug in the solid state cannot infer the same compatibility in solution.

The decision to develop a solution, syrup or a suspension of a drug is influenced by many factors like solubility and the desired release profile of the drug and properties of the base vehicle, such as surface tension, viscosity, boiling point, and specific heat of solution, all of which may be affected in various ways. In case of clear liquids, lack of solubility of the drug in the base vehicle may demand the need for miscible co-solvents. Similarly, a miscible solvent may be needed to decrease the solubility of the drug in a primary vehicle in formulating a suspension.

The therapeutic utility of drugs involves the application of dosage forms/delivery systems, which serve as carrier systems together with several excipients to deliver the active therapeutic agent to the site of action. Suspensions are an important class of pharmaceutical dosage forms that may be given by many routes, including oral, topical, parenteral, and also used in the eye for ophthalmic purposes. Surprisingly, large proportions of new drug candidates that are emerging are predominantly water insoluble and, therefore, demonstrate poor bioavailability in the solution dosage form. While suspensions present a viable formulation option for many drugs, particularly for water insoluble, hydrophobic drug substances, there are certain criteria that a well-formulated suspension should meet.

The suspension dosage form has long been used for poorly soluble active ingredients for various therapeutic indications.

Pharmaceutical solutions, where the active pharmaceutical ingredient is soluble offer certain advantages, including stability, uniformity in dosing, etc. Thus, more and better pharmaceutical solution platforms are desirable.

Therefore, looking at the need existing in the art for the preparation of liquid pharmaceutical compositions of various drugs to mask its taste and make them overall more acceptable to all types of patient population, this disclosure contemplates pharmaceutical solutions having palatability and acceptability along with prolonged stability. These properties of the liquid compositions of the present invention make them favorable for use in the pharmaceutical industry.

SUMMARY

In some embodiments, the pharmaceutical composition comprises an active pharmaceutical ingredient (API), a buffering agent, and water, wherein the pH of the composition is between about pH 5 and about pH 8. In some embodiments, the active pharmaceutical ingredient is selected from ramipril, solifenacin, vigabatrin, losartan potassium, warfarin, and melatonin. In some embodiments, the pH of the composition is between about 6 to about 7. In some embodiments, the pharmaceutical composition is an aqueous solution.

In some embodiments, the buffering agent is selected from acetic acid, adipic acid, ammonium carbonate, ammonium hydroxide, ammonium phosphate, boric acid, citric acid, diethanolamine, fumaric acid, hydrochloric acid, lactic acid, malic acid, nitric acid, propionic acid, potassium acetate, potassium bicarbonate, potassium chloride, potassium citrate, potassium metaphosphate, potassium phosphate, sodium acetate, sodium bicarbonate, sodium borate, sodium carbonate, sodium chloride, sodium citrate, sodium glycolate, sodium hydroxide, sodium lactate, sodium phosphate, sodium dihydrogen phosphate, disodium hydrogen phosphate, sodium propionate, succinic acid, sulfuric acid, tartaric acid, triethylamine, triethanolamine, tromethamine, trolamine, and salts thereof, and any combinations thereof.

In some embodiments, the pH of the composition is between is pH 5-8 or between pH 6-7.

DETAILED DESCRIPTION

Generally, disclosed herein are pharmaceutical compositions in the form of a solution for oral delivery. Particularly, the solution includes a buffering agent and water, in addition to the water-soluble active pharmaceutical ingredient. Additional excipients may also be used. The buffering agent is used to achieve the desired pH, depending on the active pharmaceutical ingredient.

Because of their liquid character, liquid dosage forms represent an ideal dosage form for patients who have difficulty swallowing tablets or capsules. This factor is of particular importance in administration of drugs to children and aged patients. The liquid dosage forms disclosed herein are useful for administering to pediatric and geriatric patients.

The solution dosage form can be a viable alternative for patients who have problems with swallowing the tablet or capsule dosage form. It provides assurance of dosage uniformity upon administration to patients and eliminates difficulty of administration. A solution can also provide physicians more flexibility in designing dosage regimens for patients. Solution dosage form of an antiepileptic drug is suitable for administration to both pediatric and geriatric patients while also compensating for a good organoleptic properties and remaining suitably stable. Hence, the development of a liquid formulation is desirable since it offers improved patient compliance. The solution dosage forms according to the present invention comprises a pharmaceutically active agent or pharmaceutically acceptable salt thereof and one or more pharmaceutically acceptable excipients or additives selected from the group comprising of vehicles, solvents/co-solvents, solubilizers, surfactants, buffering agents and/or pH modifying agents and/or buffering agents or any combination thereof. The solution dosage forms according to the present invention may further comprise one or more agents selected from the group comprising of preservatives, sweetening agents, flavoring agents and coloring agents or any combination thereof.

In some embodiments, the liquid pharmaceutical solutions have palatability, prolonged stability and improved and/or comparable pharmacokinetic profile or bioavailability when compared to the known or marketed formulations. The liquid pharmaceutical compositions of the present invention may comprise sweetener(s) and flavoring agent(s) which masks the bitter taste of many drugs and provides pleasant taste.

This disclosure is not limited to the particular systems, devices and methods described, as these may vary. The terminology used in the description is for the purpose of describing the particular versions or embodiments only, and is not intended to limit the scope.

It must also be noted that as used herein and in the appended claims, the singular forms "a," "an," and "the" include plural reference unless the context clearly dictates otherwise. Thus, for example, reference to a "surfactant" is a reference to one or more surfactants and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with an active pharmaceutical ingredient, can include, but is not limited to, providing the active pharmaceutical ingredient into or onto the target tissue; or providing the active pharmaceutical ingredient systemically to a patient by, e.g., intravenous injection whereby the therapeutic reaches the target tissue. "Administering" a composition may be accomplished by injection, topical administration, orally, or by either method in combination with other known techniques. In some embodiments, administering is through an oral route of administration.

The term "subject" as used herein includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The term "improve" is used to convey that the compounds of embodiments herein change either the appearance, form, characteristics and/or the physical attributes of the tissue to which it is being provided, applied or administered.

The term "inhibit" includes the administration of a compound of embodiments herein to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

As used herein, the term "therapeutic" means an agent utilized to treat, combat, inhibit, ameliorate, prevent or improve an unwanted condition or disease of a patient.

A "therapeutically effective amount" or "effective amount" of a composition is a predetermined amount calculated to achieve the desired effect. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, concomitant therapies and the condition being treated. However, it will be understood that the effective amount administered will be determined by the physician in the light of the relevant circumstances including the condition to be treated, the choice of compound to be administered, and the chosen route of administration, and therefore the above dosage ranges are not intended to limit the scope of embodiments herein in any way. A therapeutically effective amount of a compound of this disclosure is typically an amount such that when it is administered in a physiologically tolerable excipient composition, it is sufficient to achieve an effective systemic concentration or local concentration in the tissue.

The terms "treat," "treated," or "treating," as used herein, refers to both therapeutic treatment and prophylactic or preventative measures, wherein the object is to inhibit, prevent or slow down (lessen) an undesired physiological condition, disorder or disease, or to improve, inhibit, or otherwise obtain beneficial or desired clinical results. For the purposes of this invention, beneficial or desired clinical results include, but are not limited to, improvement or alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

As used herein, the term "a derivative thereof" refers to a salt thereof, a pharmaceutically acceptable salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof. In some embodiments, the active pharmaceutical ingredient may be administered as a derivative thereof.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera As a non-limiting example, each range discussed herein can be readily broken down into a lower third, middle third and upper third, et cetera As will also be understood by one skilled in the art all language such as "up to," "at least," and the like include the number recited and refer to ranges which can be subsequently broken down into subranges as discussed above. Finally, as will be understood by one skilled in the art, a range includes each individual member.

The weight percentages disclosed herein may be weight-to-weight, weight-to-volume, or volume-to-volume percentages, as appropriate.

Disclosed herein are the pharmaceutical compositions comprising an active pharmaceutical ingredient, a buffering agent, and water, wherein the pH of the composition is between about pH 5 to about pH 8. In some embodiments, the pharmaceutical composition is an aqueous solution suited for oral delivery.

Typically, the active pharmaceutical ingredient (API) for use in the pharmaceutical composition disclosed herein are water-soluble at a pH of between about 5 and about 8. In some instances, the active pharmaceutical ingredient is water-soluble at a pH of less than about 7. Reference to the active pharmaceutical ingredient also refers to salt and other forms of the active. The examples herein present specific dosage formulations for the exemplary actives, one of ordinary skill in the art will recognize these doses can be adjusted as needed, without varying from the scope and spirit of this disclosure.

In some embodiments, the active pharmaceutical ingredient is selected from ramipril, solifenacin, vigabatrin, losartan potassium, warfarin, and melatonin. Other active pharmaceutical ingredients that may be present in the composition include divaprex, phenobarbital, methlyphenobarbital, metharbital, barbexaclone, stiripentol, clobazam, clonazepam, clorazepate, diazepam, midazolam, lorazepam, nitrazepam, temazepam, nimetazepam, potassium bromide, felbamate, carbamazepine, oxcarbazepine, progabide, tiagabine, gabapentin, pregabalin, ethotoin, phenytoin, mephenytoin, fosphenytoin, paramethadione, trimethadione, ethadione, beclaminde, primidone, brivaracetam, levetiracetam, seletracetam, ethsuximide, phesuximide, mesuximide, acetazolamide, sulthiame, methazolamide, and combination thereof.

Solifenacin (empirical formula $C_{23}H_{26}N_2O_2$ and a molecular weight of 480.55), also known as (3R)-1-azabicyclo[2.2.2]octan-3-yl (1S)-1-phenyl-1,2,3,4-tetrahydroisoquinoline-2-carboxylate, has the chemical structure as follows:

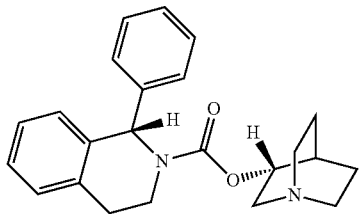 [SMILES: O=C(O[C@H]1CN2CCC1CC2)N1CCc2ccccc2[C@@H]1c1ccccc1]

Solifenacin is a medication of an anti-muscarinic class, used for treating contraction of overactive bladder with symptoms of increased urination frequency and urge incontinence. It is a competitive cholinergic receptor antagonist. Solifenacin is M3-receptor selective antagonist which may be more bladder-specific with reduced tendency for anticholinergic side effects. Solifenacin prevents the binding of acetylcholine to this receptor, and reduces smooth muscle tone in the bladder, allowing the bladder to retain larger volumes of urine and reducing the number of micturition, urgency and incontinence episodes. Solifenacin is available in the market under the brand name VESICARE. Solifenacin is a bladder relaxant and useful in treating overactive bladder.

Vigabatrin is useful as an anticonvulsant, particularly in the treatment of epilepsy, seizures, partial onset seizures, seizures associated with Lennox-Gastaut syndrome, spasms associated with West syndrome, and generalized tonic-clonic seizures.

Ramipril is an ACE inhibitor useful as a hypertensive agent.

Melatonin is a hormone useful for a wide variety of treatments such as for regulating circadian rhythm, regulation of the inflammatory response, treatment of systemic inflammatory response syndrome (SIRS), treatment the multiple organ dysfunction syndrome (MODS), the treatment of sepsis in neonates, treatment of sepsis in adults, the treatment of myocardial infarction, the treatment of mitochondrial damage, treatment of pulmonary edema, treatment failure kidney or liver, or treating oxidative stress situation generated during surgery, and particularly during abdominal surgery.

In some embodiments, the active pharmaceutical ingredient is present in the pharmaceutical composition in an effective amount from about 1 mg/mL to about 350 mg/mL, about 1 mg/mL to about 300 mg/mL, about 1 mg/mL to about 250 mg/mL, about 1 mg/mL to about 200 mg/mL, about 1 mg/mL to about 150 mg/mL, about 1 mg/mL to about 100 mg/mL, about 1 mg/mL to about 50 mg/mL, about 1 mg/mL to about 25 mg/mL, about 1 mg/mL to about 20 mg/mL, about 1 mg/mL to about 15 mg/mL, about 1 mg/mL to about 10 mg/mL, or about 1 mg/mL to about 5 mg/mL, and values in-between any of these ranges. Specific examples include about 1 mg/mL, about 10 mg/mL, about 12 mg/mL, about 14 mg/mL, about 16 mg/mL, about 18 mg/mL, about 20 mg/mL, about 22 mg/mL, about 25 mg/mL, about 27 mg/mL, about 30 mg/mL, about 40 mg/mL, about 50 mg/mL, about 60 mg/mL, about 70 mg/mL, about 80 mg/mL, about 90 mg/mL, about 100 mg/mL, about 150 mg/mL, about 200 mg/mL, about 250 mg/mL, about 300 mg/mL, or about 350 mg/mL.

In some embodiments, the active pharmaceutical ingredient is present in an effective amount in the composition from about 0.1 wt % to about 50 wt %, about 0.1 wt % to about 40 wt %, about 0.1 wt % to about 30 wt %, about 0.1 wt % to about 20 wt %, about 0.1 wt % to about 10 wt %, about 0.1 wt % to about 5 wt %, about 0.1 wt % to about 3 wt %, or about 0.1 wt % to about 1 wt %, or any of the values between these ranges. Specific examples include 0.1 wt %, 0.5 wt %, about 1 wt %, about 2 wt %, about 3 wt %, about 5 wt %, about 10 wt %, about 15 wt %, about 20 wt %, about 25 wt %, about 30 wt %, about 35 wt %, about 40 wt %, about 45 wt %, or about 50 wt %. In some embodiments, the weight percentages disclosed herein may be volume-to-volume or weight-to-volume percentages. In some embodiments, the active pharmaceutical composition is vigabatrin.

In some embodiments, the active pharmaceutical ingredient is present in the composition at least above 1 wt %, at least above 2 wt %, at least above 3 wt %, at least above 4 wt %, at least above 5 wt %, at least above 6 wt %, at least above 7 wt %, at least above 8 wt %, at least above 9 wt %, or at least above 10 wt %. In some embodiments, the active pharmaceutical ingredient is vigabatrin.

In some embodiments, the pharmaceutical composition surprisingly comprises high concentration of active pharmaceutical ingredient, such as about 5 wt %, about 6 wt %, about 7 wt %, about 8 wt %, about 9 wt %, about 10 wt %, about 15 wt %, or about 20 wt %. In some embodiments, the active pharmaceutical ingredient is vigabatrin.

In some embodiments, the pharmaceutical composition comprises one or more buffering agents selected from acetic acid, adipic acid, ammonium carbonate, ammonium hydroxide, ammonium phosphate, boric acid, citric acid, diethanolamine, fumaric acid, hydrochloric acid, lactic acid, malic acid, nitric acid, propionic acid, potassium acetate, potassium bicarbonate, potassium chloride, potassium citrate, potassium metaphosphate, potassium phosphate, sodium acetate, sodium bicarbonate, sodium borate, sodium carbonate, sodium chloride, sodium citrate, sodium glycolate, sodium hydroxide, sodium lactate, sodium phosphate, sodium dihydrogen phosphate, disodium hydrogen phosphate, sodium proprionate, succinic acid, sulfuric acid, tartaric acid, triethylamine, triethanolamine, tromethamine, trolamine, and salts thereof, and any combinations thereof. In some embodiments, a phosphate buffer system is used in the compositions. In some embodiments, a phosphate/citrate buffer system is used in the compositions. Specific examples of the pH levels of the composition include about pH 5 to about pH 8, about pH 5 to about pH 7.5, about pH 5 to about pH 7, about pH 5 to about pH 6.5, about pH 5 to about pH 6, about pH 5 to about pH 5.5, about pH 5.5 to about pH 8, about pH 6 to about pH 8, about pH 6.5 to about pH 8, about pH 7 to about pH 8, about pH 7.5 to about pH 8, about pH 6 to about pH 7, about pH 6 to about pH 7.5, about pH 6 to about pH 8, about pH 5 to about pH 7, about pH 5.5 to about pH 7, and ranges between any two of these values. Non-limiting examples include about pH 5, about pH 5.2, pH 5.5, about pH 5.7, about pH 6, about pH 6.1, about pH 6.2, about pH 6.3, about pH 6.4, about pH 6.5, about pH 6.6, about pH 6.7, about pH 6.8, about pH 6.9, about pH 7, about pH 7.3, about pH 7.5, about pH 7.7, and about pH 8. The amount of buffering agent present to the composition may depend on the desired pH that is to be achieved. For example, the amount of the buffering agent may be present in the composition from about 0.001 wt % to about 1 wt %, about 0.001 wt % to about 0.5 wt %, about 0.001 wt % to about 0.1 wt %, or about 0.001 wt % to about 0.01 wt %.

In some embodiments, the compositors disclosed herein are aqueous solutions. In some embodiments, the only solvent that is present in the composition is water. The amount of water present in the composition may vary, and depend on the presence of other ingredients in the composition. In some embodiments, water is added q.s. to the composition. In some embodiments, water is present in the composition from about 30 wt % to about 90 wt %, about 30 wt % to about 80 wt %, about 30 wt % to about 70 wt %, about 30 wt % to about 60 wt %, about 30 wt % to about 50 wt %, or about 30 wt % to about 40 wt %.

In some embodiments, the compositions do not contain any polyhydric alcohols having 2 to 6 carbon atoms and 2 to 6 hydroxyl groups.

Other known pharmaceutical excipients may be used in the ordinary amounts for then-normal purposes, so long as they do not negatively affect the effectiveness or stability of the suspensions. Examples of additional excipients that may be present in the composition include but not limited to fillers/vehicles, solvents/co-solvents, preservatives/antioxidants, suspending agents, surfactants, antifoaming agents, buffering agents, chelating agents, sweeteners, flavoring agents, sweetness/flavor enhancing agents, or combinations thereof. In some embodiments, the pharmaceutical excipient is in an amount of about 0.1 wt % to about 50 wt %, about 0.5 wt % to about 50 wt %, about 1 wt % to about 50 wt %, about 2 wt % to about 50 wt %, about 3 wt % to about 50 wt %, about 4 wt % to about 50 wt %, about 5 wt % to about 50 wt %, about 6 wt % to about 50 wt %, about 7 wt % to about 50 wt %, about 8 wt % to about 50 wt %, about 9 wt % to about 50 wt %, about 10 wt % to about 50 wt %, about 20 wt % to about 50 wt %, or a range of any two of these values.

In some embodiments, the pharmaceutical composition comprises flavoring agents. Non-limiting examples of flavoring agents that may be present in the composition include synthetic flavor oils and flavoring aromatics and/or natural oils, extracts from plants leaves, flowers, fruits, and so forth and the like or any combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, strawberry flavor, tutti-fruity flavor, mint flavor, or any combinations thereof. Solid forms, such as spray dried forms of flavoring agents, may also be useful in the Liquid dosage forms disclosed herein. In some embodiments, the flavoring agent is tutti-fruity flavor. Flavoring agents may be present from about 0.001 wt % to about 5 wt % of the total composition, about 0.001 wt % to about 4 wt % of the total composition, about 0.001 wt % to about 3 wt % of the total composition, about 0.001 wt % to about 2 wt % of the total composition, or about 0.001 wt % to about 1 wt % of the total composition.

In some embodiments, the pharmaceutical composition comprises sweetening agents. Several of the commonly used sweetening agents are ionic and have the potential to interact with other components of the suspension. Some sweetening agents are more stable than others in aqueous solution. These factors may be important in the final selection of the sweetening agent. Non-limiting examples of sweetening agents that may be present in the composition are glucose, sucralose, maltitol, trehalose, fructose, xylose, dextrose, galactose, tagatose, maltose, sucrose, glycerol, dulcitol, mannitol, lactitol, sorbitol, xylitol, saccharine or the corresponding sodium, potassium or calcium salt, cyclamate or the corresponding sodium or calcium salt, aspartame, acesulfame or the potassium salt thereof, dulcin, ammonium glycyrrhizinate, alitame, inulin, isomalt, neohesperidin dihydrochalcone, thaumatin, or any combinations thereof. Sweetening agents may be present from about 0.01 wt % to about 40 wt % of the total composition, about 0.01 wt % to about 20 wt % of the total composition, about 0.01 wt % to about 10 wt % of the total composition, about 0.01 wt % to about 5 wt % of the total composition, or about 0.01 wt % to about 1 wt % of the total composition.

In some embodiments, the pharmaceutical composition comprises preservatives. Preservatives are compounds which are included in the compositions to prevent the growth of microorganisms during the product's manufacture and shelf life. Examples of the suitable preservatives are, but not limited to, benzyl alcohol, chloro-butanol, chloro-cresol, alkyl esters of parabens, phenol, phenyl ethanol, benzoic acid, potassium sorbate, sodium benzoate and antimicrobial solvents like propylene glycol, chloroform, or a combination thereof. In some embodiments, the composition comprises a preservative selected from propyl 4-hydroxy benzoate, methyl 4-hydroxy benzoate, or a combination thereof. Preservatives may be present in the composition from about 0.001 wt % to about 1 wt % of the total composition, about 0.001 wt % to about 0.5 wt % of the total composition, about 0.001 wt % to about 0.1 wt % of the total composition, or about 0.001 wt % to about 0.01 wt % of the total composition.

In some embodiments, the pharmaceutical composition comprises antioxidants. Antioxidants are substances capable of inhibiting oxidation and that may be added to pharmaceutical products to prevent deterioration by oxidative processes. Examples of suitable antioxidants are but not limited to butylatedhydroxyanisole (BHA), butylatedhydroxy toluene (BHT), sodium metabisulfite, ascorbic acid, alphatocopherol, sodium edetate, or any combination thereof. In some embodiments, the antioxidants are BHA and BHT.

In some embodiments, the pharmaceutical composition comprises about 0.1 wt % to about 20 wt % of an active pharmaceutical ingredient, water, and one or more buffering agents in a quantity to achieve a pH of about 5 to 8.

In some embodiments, the pharmaceutical composition comprises about 0.1 wt % to about 20 wt % of vigabatrin, water, and one or more buffering agents in a quantity to achieve a pH of about 5 to 8.

In some embodiments, the pharmaceutical composition comprises about 0.1 wt % to about 20 wt % of vigabatrin, water, and one or more buffering agents in a quantity to achieve a pH of about 6 to 7.

In some embodiments, APIs in the compositions disclosed herein are stable for extended periods of time. For example, in some embodiments, APIs in the compositions are stable at temperature ranges from about 4° C. to about 50° C. for a period of 12-36 months. In some embodiments, APIs in the compositions are stable at temperature ranges from about 4° C. to about 45° C. for a period of 12-36 months. In some embodiments, APIs in the compositions are stable at temperature ranges from about 4° C. to about 40° C. for a period of 12-36 months. In some embodiments, APIs in the compositions are stable at temperature ranges from about 4° C. to about 35° C. for a period of 12-36 months. In some embodiments, APIs in the compositions are stable at temperature ranges from about 4° C. to about 30° C. for a period of 12-36 months.

In some embodiments, the pharmaceutical compositions disclosed herein are useful for the manufacture of a medicament. In one of the further embodiments, the pharmaceutical compositions disclosed herein are useful as a medicament.

In some embodiments, the active pharmaceutical ingredient may be administered in combination with one or more additional active pharmaceutical ingredients. In some embodiments, the pharmaceutical compositions disclosed herein may include an additional active pharmaceutical ingredient. In some embodiments, the pharmaceutical compositions disclosed herein may be administered in conjunction with, either concurrently or sequentially, with the additional active pharmaceutical ingredient.

Method of Treatment

Some embodiments are directed to a methods of using the pharmaceutical composition of embodiments herein for the treatment of diseases or disorders. In some embodiments, a method of treating a disease or a disorder in a subject in need thereof comprises administering to the subject the pharmaceutical composition of embodiments disclosed herein. In some embodiments, the disease or disorder comprises seizures, partial onset seizures, seizures associated with Lennox-Gastaut syndrome, spasms associated with West syndrome, generalized tonic-clonic seizures, epilepsy, or a combination thereof. In some embodiments, the pharmaceutical composition comprises vigabatrin.

In some embodiments, a method of treating a seizure in a subject in need thereof comprises administering to the subject a pharmaceutical composition disclosed herein, wherein the active pharmaceutical ingredient present in the composition is vigabatrin.

In some embodiments, a method of treating epilepsy in a subject in need thereof comprises administering to the subject a pharmaceutical composition disclosed herein, wherein the active pharmaceutical ingredient present in the composition is vigabatrin.

In other embodiments, methods of administration may include, but are not limited to, intravascular injection, intravenous injection, intraarterial injection, intratumoral injection, intraperitoneal injection, subcutaneous injection, intramuscular injection, transmucosal administration, oral administration, topical administration, local administration, or regional administration. In some embodiments, the administration is by oral route.

In some embodiments, the compositions disclosed herein may be administered once, as needed, once daily, twice daily, three times a day, once a week, twice a week, every other week, every other day, or the like for one or more dosing cycles. A dosing cycle may include administration for about 1 week, about 2 weeks, about 3 weeks, about 4 weeks, about 5 weeks, about 6 weeks, about 7 weeks, about 8 weeks, about 9 weeks, or about 10 weeks. After this cycle, a subsequent cycle may begin approximately 1, 2, 3, 4, 5, 6, 7, 8, 9, 10, 11, or 12 weeks later. The treatment regime may include 1, 2, 3, 4, 5, or 6 cycles, each cycle being spaced apart by approximately 1, 2, 3, 4, 5, 6, 7, 8, 9, 10, 11, or 12 weeks.

The pharmaceutical compositions disclosed herein may have unexpectedly dramatic dissolution profiles. Rapid dissolution of an administered active pharmaceutical ingredient is preferable, as faster dissolution generally leads to greater bioavailability and faster onset of action. To improve the dissolution profile and bioavailability of an active pharmaceutical ingredient, it would be useful to increase dissolution of the active pharmaceutical ingredient used so that it could attain a level close to 100% dissolution of the drug substance.

In some embodiments, the pharmaceutical compositions disclosed herein comprising the active pharmaceutical ingredient or derivative thereof, exhibit improved or comparable pharmacokinetic profiles when compared to marketed or known compositions of the same active pharmaceutical ingredient or derivative thereof. For example, the Cmax and/or AUC of the pharmaceutical compositions of disclosed herein can be greater than or substantially equal to the Cmax and/or AUC for known or marketed compositions, e.g. solid formulations, administered at the same dose. In addition, the Tmax of the pharmaceutical compositions disclosed herein can be lower than or substantially equal to that obtained for a known or marketed composition, administered at the same dose. In addition, combinations of an improved or comparable Cmax, AUC and Tmax profile can be exhibited by the pharmaceutical compositions disclosed herein, as compared to known or marketed compositions. In further aspects, the pharmaceutical compositions disclosed herein may result in minimal different absorption levels when administered under fed as compared to fasting conditions.

In some embodiments, the pharmaceutical compositions disclosed herein may exhibit a Tmax not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the Tmax exhibited by a marketed or known formulation, when administered at a same dose.

In some embodiments, the pharmaceutical compositions disclosed herein may exhibit a Cmax which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the Cmax exhibited by a marketed or known formulation, when administered at a same dose.

In some embodiments, the pharmaceutical compositions disclosed herein may exhibit an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least 5 about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by a marketed or known formulation, when administered at a same dose.

In some embodiments, the Tmax of the active pharmaceutical ingredient or salt thereof used fix the preparation of the pharmaceutical compositions disclosed herein, when assayed in the plasma of the mammalian subject is less than about 6 to about 8 hours. In other embodiments, the Tmax of the active pharmaceutical ingredient or salt thereof is less than about 6 hours, less than about 5 hours, less than about 4 hours, less than about 3 hours, less than about 2 hours, less than about 1 hour, or less than about 30 minutes after administration.

In some aspects, the pharmaceutical compositions disclosed herein exhibit improved or comparable bioavailability as compared to known or marketed compositions.

Reference to the active pharmaceutical ingredient also refers to salt and other forms of the active. The examples herein present specific dosage formulations for the exemplary actives, one of ordinary skill in the art will recognize these doses can be adjusted as needed, without varying from the scope and spirit of this disclosure.

EXAMPLES

Example 1: Pharmaceutical Solution Including Solifenacin

Solifenacin Oral Solution 10 mg/15 ml

TABLE 1

| Sr. No. | Ingredients | Quantity (mg/mL) |
|---|---|---|
| 1. | Solifenacin succinate* | 2.000 |
| 2. | Sodium benzoate | 0.200 |
| 3. | Sucralose | 1.000 |
| 4. | Liquid maltitol | 400.000 |

TABLE 1-continued

| Sr. No. | Ingredients | Quantity (mg/mL) |
|---|---|---|
| 5. | Peppermint flavor | 0.100 |
| 6. | Citric acid monohydrate* | Qs |
| 7. | Purified water | Qs to ml |

Solifenacin Oral Solution 5 mg/5 ml

TABLE 2

| Sr. No. | Ingredients | Role of excipients | Formulation composition (mg/mL) | Formulation composition (% w/v) |
|---|---|---|---|---|
| 1 | Solifenacin succinate | Active | 1 | 0.1 |
| 2 | Sodium benzoate | Preservative | 0.2 | 0.02 |
| 3 | Sucralose | Sweetener | 1 | 0.1 |
| 4 | Liquid maltitol | Sweetener | 400 | 40 |
| 5 | Peppermint flavor | Flavour | 0.1 | 0.01 |
| 6 | Citric acid monohydrate | buffering agent | pH 4.0-5.0 | pH 4.0-5.0 |
| 7 | Purified water | Vehicle | q.s to 1 ml | q.s to 100 ml |

The oral solifenacin solutions above composition are prepared by following steps but not limited to:
(a) take required quantity of water; (b) mix one or more excipients until dissolved; (c) adjust to desired pH by adding buffering agent; and (d) add required quantity of vigabatrin and mix until dissolved.

Example 2: Stability Data for Solifenacin

TABLE 3

| Tests | Initial | 40 ± 2° C./ 75% RH 6M | 25 ± 2° C./ 65% RH 6M |
|---|---|---|---|
| Description | A clear colorless solution | A clear colorless solution | A clear colorless solution |
| pH | 4.66 | 4.35 | 4.4 |
| Assay (%) | 101 | 99.3 | 98.8 |
| Assay of Sodium benzoate (%) | 101 | 99.4 | 98.7 |
| Related substances | | | |
| Isoquiniline impurity (%) | ND | ND | ND |
| Unknown Impurity (%) | ND | 0.14 | BQL |
| Total Impurities (%) | ND | 0.14 | BQL |

Example 3: Bioequivalent Study

"Bioequivalence study" denotes a scientific basis on which generic and brand name drugs are compared with one another. Drugs are bioequivalent if they enter circulation at the same rate when given in similar doses under similar conditions. Parameters often used in bioequivalence studies are Cmax, AUCO-infinity, AUCO-t.

The pharmaceutical composition prepared as per the example above was subjected to a bioequivalence study in healthy human subjects. The test was carried out by administering test product with respect to reference product. The test product of the present invention pharmaceutical composition was found bioequivalent to reference product as test product is considered bioequivalent with a reference product, when AUCO-1 and Cmax is within 80-125% of the reference product, including the 90% confidence interval.

The below table represents the bioequivalence data of the composition of the present invention:

TABLE 4

| Pharmacokinetic Parameters (Units) | Ln- transformed Geometric Least Squares Mean | | T/R (%) | 90% Confidence Interval | |
|---|---|---|---|---|---|
| | Test Product(T) | Reference Products (R) | | Lower | Upper |
| $C_{max}$ (ng/mL) | 19.0194 | 17.1162 | 111.12 | 105.49 | 117.04 |
| $AUC_{0-72h}$ (ng · hr/mL) | 758.2960 | 697.1407 | 108.77 | 103.98 | 113.79 |

Reference Product (R): VESICARE 10 mg film-coated tablet
Test Product (T): Oral solution of Solifenacin succinate (1 mg/ml)
In the present context "$C_{max}$" denotes the maximal plasma concentration after administration of the drug;
$AUC_{0-72h}$ is the area under the plasma concentration versus time curve from time 0 to time 72 hrs at steady state conditions.

Example 4: Pharmaceutical Solution of Melatonin

General formula of the composition of the invention is below:

TABLE 5

| Ingredient | Quantity (mg/mL) |
|---|---|
| Melatonin | 0.1-10 |
| Preservative | 0.01-10 |
| Buffering agent | Q.S to pH 3-7 |
| Sweetening agent | 0.1-100 |
| Flavouring agent | 0.001-10 |
| Vehicle | Q.S to 1 ml |

A general process for the preparation of the pharmaceutical composition according to the present invention is described below:
(a) Add water and adjust desirable pH using the buffering agent; (b) add melatonin and mix till it dissolves; (c) add sweetening agent and flavouring agent; and (d) adjust volume to desirable batch size.

A more specific formulation of melatonin solution is described below;

TABLE 6

| Sr. No. | Ingredients | Role of excipients | Formulation composition % w/v | Formulation composition (mg/mL) |
|---|---|---|---|---|
| 1 | Melatonin# | Active | 0.1 | 1 |
| 2 | Sodium benzoate | Preservative | 0.0625 | 0.625 |
| 3 | Citric acid monohydrate | buffering agent (pH 4.0-5.0) | 0.035 | 0.35 |
| 4 | Sucralose | Sweetener | 0.1 | 1 |
| 5 | Strawberry flavor | Flavour | 0.01 | 0.1 |
| 6 | Purified water | Vehicle | q.s to 100 ml | Qs. to 1 mL |

Method of Preparation: A liquid oral pharmaceutical composition comprising Melatonin as active ingredient and Sodium benzoate, Citric acid monohydrate, Sucralose, Strawberry flavour and Purified water was prepared following below mentioned process comprising steps of:
(a) add required quantity of purified water and adjust desirable pH using required quantity of citric acid monohydrate; (b) add required quantity of melatonin into the mixture obtained in step (a) and mix till it dissolves; (c) add required quantity of sucralose and strawberry flavor into the mixture obtained in step (b); and (d) adjust volume to desirable batch size with purified water.

Example 5: Stability Data for Solution Including Melatonin

The oral liquid pharmaceutical composition prepared according to Example 1 exhibits unexpected stability profile when tested after three (3) months under the conditions 40±2° C./25% RH and 25±2° C./60% RH. The liquid composition according to the present invention possess very less amount of impurities and highest degree of purity. The results of the stability tests conducted are summarized in the table below.

TABLE 7

| Tests | Initial | 40 ± 2° C./ 75° RH 3M | 25 ± 2° C./ 60%. RH 3M |
|---|---|---|---|
| Description | A clear colorless solution | A clear colorless solution | A clear colorless solution |
| pH | 4.32 | 4.31 | 4.29 |
| Assay (%) | 99.6 | 97.8 | 98.3 |
| Assay of Sodium benzoate (%) | 98.7 | 99.3 | 99 |
| Related substances | | | |
| Unknown Impurity (%) | BQL | 0.06 | BQL |
| Total Impurities (%) | 0.06 | 0.13 | BQL |

Example 6: Pharmaceutical Composition of Ramipril

TABLE 8

| Sr. No. | Ingredients | Role of ingredients | Formulation composition % w/v | (mg/ml) |
|---|---|---|---|---|
| 1 | Ramipril # | Active | 0.05 | 0.5 |
| 2 | Methyl parahydroxybenzoate# | Preservative | 0.18 | 1.8 |
| 3 | Ethyl parahydroxybenzoate# | Preservative | 0.012 | 0.12 |
| 4 | Sucralose | Sweetener | 0.05 | 0.5 |
| 5 | Citric acid monohydrate | buffering agent | q.s to pH 3.0-4.0 | q.s to pH 3.0-4.0 |
| 6 | Frozen peppermint flavor | Flavour | 0.01 | 0.1 |
| 7 | Purified Water | Vehicle | q.s to 100 ml | Q.S. 1 ml |

The oral pharmaceutical solution of above composition is prepared by following method:
a) 80% of purified water taken in stainless steel vessel, heated to 80-85° and under continuous stirring methyl paraben, ethyl paraben were added and allow to cool at room temperature.
b) To above clear solution weighed quantity of API were added slowly and stirred for homogeneity.
c) To above prepared solution sucralose and strawberry flavor added and stirred for homogeneity.
d) To the above prepared solution citric acid monohydrate is added dropwise to adjust targeted pH (3.0-4.0)
e) Volume make up using purified water.
f) Filter above solution using 10 micron Polypropylene filter Example 7: Stability Data for Ramipril Solution

TABLE 9

| Test parameters | Initial | 25° C./60% RH 6M | 5° C. ± 3° C. 6M |
|---|---|---|---|
| Description | Complies | Complies | Complies |
| pH | 3.20 | 3.24 | 3.17 |
| Assay of Ramipril | 96.90% | 92.50% | 97.60% |
| Content of Methyl parahydroxy benzoate | 99.60% | 98.50% | 98.80% |
| Content of Ethyl parahydroxy benzoate | 96.50% | 97.20% | 97.90% |
| Related substances | | | |
| Impurity-2 | ND | ND | ND |
| Impurity-C | ND | 0.02% | 0.02% |
| Impurity-D + Impurity-E | 0.00% | 4.52% | 0.90% |
| Single maximum unknown impurity | ND | 0.37% | ND |
| Total impurities (Excluding Impurity-D + Impurity-E) | 0.00% | 0.39% | 0.02% |

Example 8: Pharmaceutical Solution of Vigabatrin

Other embodiments are directed to formulations including actives which are soluble at higher pH, from about 3 to about 7. Such liquid solution comprises an aqueous solvent; a water-soluble active pharmaceutical ingredient selected from vigabatrin; and a buffering agent in sufficient quantity such that the pH is about 3 to about 7.

The same buffering agents and solvents as described above may be used, as can any pharmaceutical excipient described herein or know to those of skill in the art. An exemplary solution is disclosed below:

TABLE 10

| Sr. No | Ingredients | Role of excipients | Formulation composition % w/v | (mg/mL) |
|---|---|---|---|---|
| 1 | Vigabatrin | Active | 10 | 100 |
| 2 | Methyl 4 hydroxy benzoate | Preservative | 0.11 | 1.1 |
| 3 | Propyl 4 hydroxy benzoate | Preservative | 0.011 | 0.11 |
| 4 | Sodium dihydrogen phosphate dihydrate | Buffering agent | 0.106 | 1.06 |
| 5 | Disodium hydrogen phosphate dihydrate | Buffering agent | 0.056 | 0.56 |
| 6 | Liquid maltitol | Sweetener | 20 | 200 |
| 7 | Sucralose | Sweetener | 0.1 | 1 |
| 8 | Frozen peppermint Flavour | Flavour | 0.01 | 0.1 |
| 9 | Purified water | Vehicle | q.s to 100 ml | Q.S to ml |

Example 9: Stability Data for Vigabatrin Solution

TABLE 11

| Test parameters | Initial | 40° C. ± 2° C./ 25% ± 5% RH 3M | 25° C. ± 2° C./ 40% ± 5% RH 3M |
|---|---|---|---|
| Description | Clear colourless solution | Clear colourless solution | Clear colourless solution |
| pH | 6.8 | 6.7 | 6.8 |
| Assay of Vigabatrin | 99.6% | 96.3% | 100.1% |
| Assay of Methyl paraben | 98.7% | 93.8% | 101.1% |
| Assay of Propyl paraben | 96.2% | 93.6% | 96.2% |
| Related substances(%) | | | |
| Bromide impurity | ND | ND | ND |
| Impurity A | 0.02% | 0.21% | 0.04% |
| Impurity B | ND | ND | ND |
| Impurity E | ND | ND | ND |
| Unspecified impurity | ND | 0.02% (RRT 0.30) | 0.02% (RRT 0.30) |
| Total impurities | 0.02% | 0.22% | 0.06% |

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Although the present invention has been described in considerable detail with reference to certain preferred embodiments thereof, other versions are possible. Therefore, the spirit and scope of the appended claims should not be limited to the description and the preferred versions contained within this specification.

What is claimed is:

1. A liquid pharmaceutical composition consisting of the following ingredients:
   a therapeutically effective amount of vigabatrin, or a pharmaceutically acceptable salt thereof, wherein the vigabatrin is present in the composition in the range from 0.1 wt % to 20 wt %;
   a preservative;
   a buffering agent;
   a sweetener;
   a flavoring agent;
   at least one of a solubilizer, a co-solvent, an antioxidant, a surfactant, an antifoaming agent, a chelating agent, a suspending agent, a viscosity builder, and a coloring agent; and
   quantum sufficit (qs.) water;
   wherein the liquid pharmaceutical composition is stable up to 3 months at room temperature with total impurities up to 3 months being less than 0.06%; wherein the total impurities are defined as the sum of any components that are not initially present in the composition at time 0 but that are present in the composition at up to 3 months.

2. The liquid pharmaceutical composition of claim 1, wherein the vigabatrin is present in an amount from 5 wt % to 15 wt % in the composition;
   the preservative is methyl 4-hydroxy benzoate, propyl 4-hydroxy benzoate, or a combination thereof;
   the buffering agent is sodium dihydrogen phosphate dihydrate, disodium hydrogen phosphate dihydrate, or a combination thereof;
   the sweetener is maltitol, sucralose, or a combination thereof; and
   the flavoring agent is selected from the group consisting of: synthetic flavor oils, flavoring aromatics, plant leave extracts, flower extracts, fruit extracts, cinnamon oil, oil of wintergreen, peppermint oils, clove oil, bay oil, anise oil, eucalyptus, thyme oil, cedar leaf oil, oil of nutmeg, oil of sage, oil of bitter almonds, cassia oil, vanilla, citrus oil, fruit essence tutti-fruity flavor, and a combination thereof.

3. The liquid pharmaceutical composition of claim 2, wherein the citrus oil is selected from the group consisting of: lemon, orange, grape, lime and grapefruit; and
   the fruit essence is selected from the group consisting of: apple, banana, pear, peach, strawberry, raspberry, cherry, plum, pineapple, apricot, and strawberry.

4. The liquid pharmaceutical composition of claim 1, wherein the pharmaceutical composition is free of polyhydric alcohol with 2 to 6 carbon atoms.

5. A liquid pharmaceutical composition comprising:
   a therapeutically effective amount of active pharmaceutical ingredient (API), at about 0.1 wt % to about 20 wt %; a preservative in the range from about 0.001 wt % to about 1 wt %; a sweetener in the range from about 0.05 wt % to about 40 wt %; a flavoring agent in the range from about 0.001 wt % to about 5 wt %; and q.s. water;
   wherein the liquid pharmaceutical composition has a pH from about pH 5 to about pH 8 and is stable up to 3 months at room temperature with total impurities up to 3 months being less than 0.06%, wherein the total impurities are defined as the sum of any components that are not initially present in the composition at time 0 but that are present in the composition at up to 3 months; and
   wherein the API consists of vigabatrin, or a pharmaceutically acceptable salt thereof.

6. The liquid pharmaceutical composition of claim 5, wherein the API is present in an amount from 5 wt % to 15 wt % in the composition;
   the preservative is methyl 4-hydroxy benzoate, propyl 4-hydroxy benzoate, or a combination thereof;
   the sweetener is maltitol, sucralose, or a combination thereof; and
   the flavoring agent is selected from the group consisting of: synthetic flavor oils and flavoring aromatics, natural oils, extracts from plants leaves, flowers, fruits, cinnamon oil, oil of wintergreen, peppermint oils, clove oil, bay oil, anise oil, eucalyptus, thyme oil, cedar leaf oil, oil of nutmeg, oil of sage, oil of bitter almonds, cassia oil, vanilla, citrus oil, fruit essence, and a combination thereof.

7. The liquid pharmaceutical composition of claim 6, wherein the citrus oil is selected from the group consisting of: lemon, orange, grape, lime and grapefruit; and
   the fruit essence is selected from the group consisting of: apple, banana, pear, peach, strawberry, raspberry, cherry, plum, pineapple, apricot, strawberry, and tutti-fruity flavor.

8. The liquid pharmaceutical composition of claim 5, wherein the pharmaceutical composition is free of polyhydric alcohol with 2 to 6 carbon atoms.

9. A liquid pharmaceutical composition comprising:
a therapeutically effective amount of vigabatrin, or a pharmaceutically acceptable salt thereof, at about 0.1 wt % to about 20 wt %; a preservative in the range from about 0.001 wt % to about 1 wt %; a sweetener in the range from about 0.05 wt % to about 40 wt %; a flavoring agent in the range from about 0.001 wt % to about 5 wt %; and q.s. water,
wherein the liquid pharmaceutical composition has a pH from about pH 5 to about pH 8 and is stable up to 3 months at room temperature with total impurities up to 3 months being less than 0.06%;
wherein the total impurities are defined as the sum of any components that are not initially present in the composition at time 0 but that are present in the composition at up to 3 months; and
with the proviso that the liquid pharmaceutical composition does not comprise any active pharmaceutical ingredient other than vigabatrin.

10. The liquid pharmaceutical composition of claim 9, wherein the vigabatrin is present in an amount from 5 wt % to 15 wt % in the composition;
the preservative is methyl 4-hydroxy benzoate, propyl 4-hydroxy benzoate, or a combination thereof;
the sweetener is maltitol, sucralose, or a combination thereof; and
the flavoring agent is selected from the group consisting of: synthetic flavor oils and flavoring aromatics, natural oils, extracts from plants leaves, flowers, fruits, cinnamon oil, oil of wintergreen, peppermint oils, clove oil, bay oil, anise oil, eucalyptus, thyme oil, cedar leaf oil, oil of nutmeg, oil of sage, oil of bitter almonds, cassia oil, vanilla, citrus oil, fruit essence, and a combination thereof.

11. The liquid pharmaceutical composition of claim 10, wherein the citrus oil is selected from the group consisting of: lemon, orange, grape, lime and grapefruit; and
the fruit essence is selected from the group consisting of: apple, banana, pear, peach, strawberry, raspberry, cherry, plum, pineapple, apricot, strawberry, and tutti-fruity flavor.

12. The liquid pharmaceutical composition of claim 9, wherein the pharmaceutical composition is free of polyhydric alcohol with 2 to 6 carbon atoms.

* * * * *